(12) United States Patent
Viens et al.

(10) Patent No.: US 10,568,777 B2
(45) Date of Patent: Feb. 25, 2020

(54) ABSORBENT TAMPON INCLUDING FIBER INTEGRATED LAYERS

(71) Applicant: The Procter & Gamble Company, Cincinnati, OH (US)

(72) Inventors: Gerard A. Viens, Wyoming, OH (US); Nery Vanesa Breslin, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 463 days.

(21) Appl. No.: 14/801,871

(22) Filed: Jul. 17, 2015

(65) Prior Publication Data
US 2016/0015572 A1    Jan. 21, 2016

Related U.S. Application Data

(60) Provisional application No. 62/026,092, filed on Jul. 18, 2014.

(51) Int. Cl.
| A61F 13/15 | (2006.01) |
| A61F 13/20 | (2006.01) |
| A61F 13/34 | (2006.01) |

(52) U.S. Cl.
CPC .... *A61F 13/2062* (2013.01); *A61F 13/15577* (2013.01); *A61F 13/15707* (2013.01); *A61F 13/15756* (2013.01); *A61F 13/34* (2013.01)

(58) Field of Classification Search
CPC .............. A61F 13/2065; A61F 13/2068; A61F 13/2085; A61F 13/34
See application file for complete search history.

(56) References Cited

U.S. PATENT DOCUMENTS

| 1,731,665 A | 10/1929 | Huebsch |
| 1,964,911 A | 7/1934 | Haas |
| 2,123,750 A | 7/1938 | Schulz |
| 2,412,391 A | 12/1946 | Crockford |
| 2,566,190 A | 8/1951 | Greiner |

(Continued)

FOREIGN PATENT DOCUMENTS

| DE | 296 15 883 U1 | 3/1997 |
| EP | 1 064 901 A2 | 1/2001 |

(Continued)

OTHER PUBLICATIONS

International Search Report and Written Opinion for (PCT/US2015/040872) dated Oct. 30, 2015.

*Primary Examiner* — Michele M Kidwell
(74) *Attorney, Agent, or Firm* — William E. Gallagher; George H. Leal

(57) ABSTRACT

A tampon has a pair of longitudinally extending side edges and an absorbent member. The absorbent member has an insertion area, a withdrawal area, and an intermediate area between the insertion area and the withdrawal area and an attachment area. The absorbent material has a plurality of fiber integrated nonwoven layers but are without fiber integration adjacent layers outboard of the attachment area. A withdrawal line extends from the withdrawal area and is attached to the absorbent member in the attachment area such that each of the plurality of absorbent layers is attached to an adjacent nonwoven layer in the attachment area.

15 Claims, 6 Drawing Sheets

(56) References Cited

U.S. PATENT DOCUMENTS

| | | | |
|---|---|---|---|
| 2,998,010 A * | 8/1961 | Griswold | A61F 13/2051 604/379 |
| 3,013,558 A | 12/1961 | Leupoid | |
| 3,037,506 A | 6/1962 | Penksa | |
| 3,058,469 A | 10/1962 | Crockford | |
| 3,101,714 A | 8/1963 | Penksa | |
| 3,135,262 A | 6/1964 | Kobler | |
| 3,420,234 A | 1/1969 | Phelps | |
| 3,431,909 A | 3/1969 | Krusko | |
| 3,572,341 A | 3/1971 | Glassman | |
| 3,628,534 A | 12/1971 | Donohue | |
| 3,674,029 A | 7/1972 | Bates | |
| 3,732,866 A | 5/1973 | Accavallo | |
| 3,738,364 A | 6/1973 | Brien et al. | |
| 3,854,481 A | 12/1974 | Messing | |
| 3,905,372 A | 9/1975 | Denkinger | |
| 3,948,257 A | 4/1976 | Bossak | |
| 3,965,905 A | 6/1976 | Schoenholz | |
| 3,995,636 A | 12/1976 | Murray | |
| 4,077,408 A | 3/1978 | Murray | |
| 4,217,900 A | 8/1980 | Wiegner | |
| 4,326,527 A | 4/1982 | Wollangk et al. | |
| 4,536,175 A | 8/1985 | Lichstein et al. | |
| 5,047,024 A | 9/1991 | Glassman | |
| 5,112,348 A | 5/1992 | Glassman | |
| 5,659,934 A | 8/1997 | Jessup et al. | |
| 5,718,675 A | 2/1998 | Leijd | |
| 5,800,338 A | 9/1998 | Kollerup | |
| 6,039,716 A | 3/2000 | Jessup et al. | |
| 6,142,984 A | 11/2000 | Brown et al. | |
| 6,186,994 B1 * | 2/2001 | Bowles | A61F 13/2068 604/385.17 |
| 6,433,246 B1 | 8/2002 | Nguyen et al. | |
| 6,554,814 B1 | 4/2003 | Agyapong | |
| 6,635,800 B2 * | 10/2003 | Jackson | A61F 13/2068 604/378 |
| 6,740,070 B2 | 5/2004 | Agyapong et al. | |
| 6,887,226 B2 * | 5/2005 | Cassoni | A61F 13/2051 604/385.18 |
| 2003/0225389 A1 * | 12/2003 | Cassoni | A61F 13/2051 604/385.18 |
| 2014/0115845 A1 * | 5/2014 | Tomsovic | A61F 13/2068 28/118 |
| 2018/0125724 A1 * | 5/2018 | Brown | A61F 13/15203 |
| 2019/0133836 A1 * | 5/2019 | Semidey-Flecha | A61F 13/208 |

FOREIGN PATENT DOCUMENTS

| | | |
|---|---|---|
| GB | 2 225 949 A | 6/1990 |
| JP | 61-073317 | 5/1986 |
| JP | 2-28900 | 8/2000 |
| JP | 2002-521133 | 7/2002 |
| WO | WO 2000/01338 | 1/2000 |
| WO | WO 2000/61052 A1 | 10/2000 |

* cited by examiner

ABSORBENT TAMPON INCLUDING FIBER INTEGRATED LAYERS

FIELD OF THE INVENTION

This invention relates to absorbent articles such as tampons. In particular, this invention relates to an improved catamenial tampon.

BACKGROUND OF THE INVENTION

A wide variety of absorbent catamenial tampons have long been known in the art. While it has been found that these tampons perform their intended function tolerably well, even the best of them do not always re-expand sufficiently, or fast enough, to provide good coverage against leakage. This failure to re-expand can lead to "bypass" failure which occurs when the menses travels along the length of the vagina without contacting the tampon, i.e., the tampon fails to intercept the flowing menses.

For ease of application, tampons are typically compressed to facilitate insertion into the vaginal cavity. While tampons can generally be compressed to a small diameter to accomplish facilitation during insertion, too much compression can inhibit the tampon's ability to re-expand once inserted into the vaginal cavity.

Accordingly, there is a need for a tampon with improved performance while maintaining or improving comfort during insertion to the wearer.

SUMMARY OF THE INVENTION

Tampons of the present invention may provide benefits to the consumer as provided herein. In some embodiments, a tampon comprises an absorbent member comprising an insertion area, a withdrawal area, and an intermediate area between the insertion area and the withdrawal area. The absorbent member further comprises an attachment area and absorbent material. The absorbent material comprises a plurality of fiber integrated nonwoven layers and are without fiber integration between adjacent fiber integrated nonwoven layers outboard of the attachment area.

A withdrawal line extends from the withdrawal area and is attached to the absorbent member in the attachment area. And, each of the plurality of absorbent layers are attached to an adjacent nonwoven layer in the attachment area.

A method of producing a tampon comprising the steps of (1) providing a plurality of fiber integrated nonwoven layers each having a basis weight of greater than about 75 grams per square meter; (2) stacking each of the plurality of fiber integrated nonwoven layers; (3) providing a withdrawal line; and (4) attaching the withdrawal line to the plurality of fiber integrated nonwoven layers in an attachment area such that each of the plurality of fiber integrated nonwoven layers is attached to an adjacent fiber integrated nonwoven layer in the attachment area.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
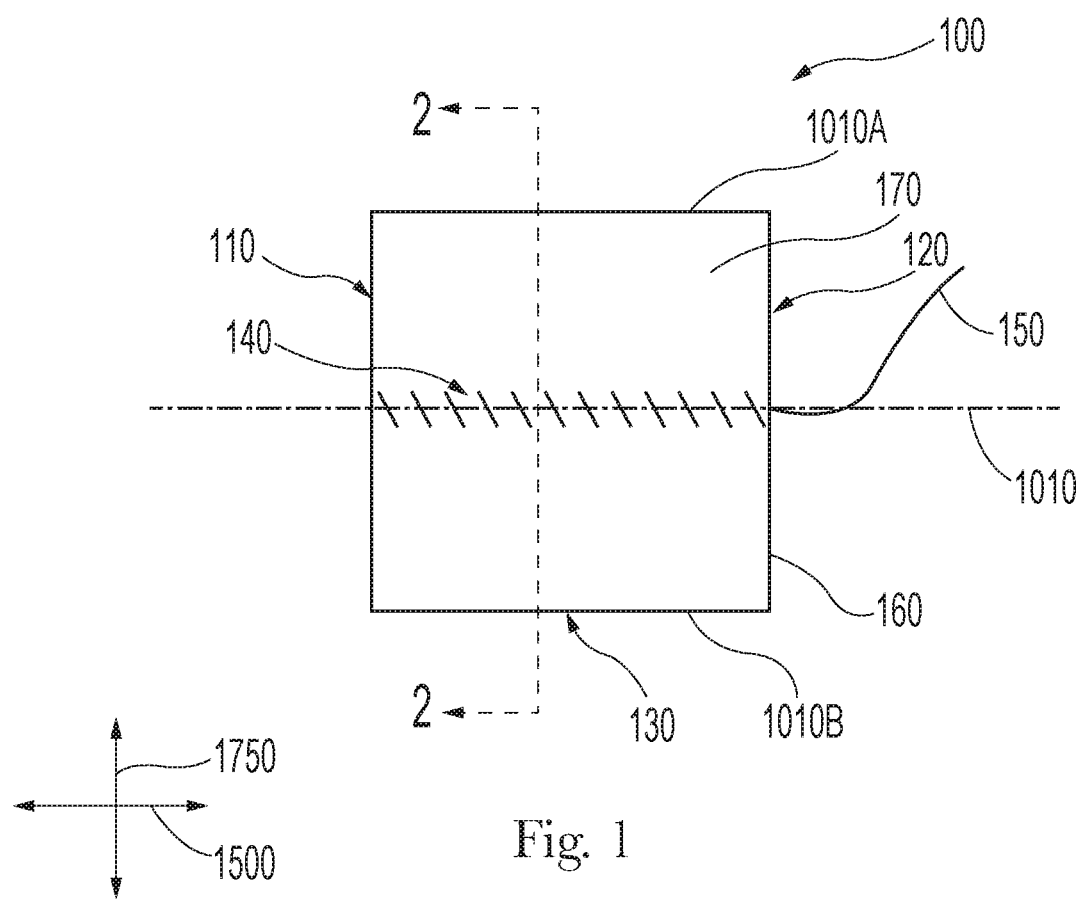
FIG. 1 is a plan view showing a tampon (in an unfolded state) constructed in accordance with the present invention.

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

As used herein, "cm" is centimeter, "mm" is millimeters, "ml" is milliliters "g" is grams, "gsm" is grams per square meter, "sec" is seconds.

As used herein "fiber integration" refers to the entanglement of fibers via mechanical processing or hydroentanglement. "Fiber integrated" shall refer to nonwoven materials which have been subjected to mechanical processing or hydroentangling. The mechanical processes or hydroentangling drive Z-direction integration of the fibers.

As used herein "hydrophilic" and "hydrophobic" have meanings as well established in the art with respect to the contact angle of a drop of water on the surface of a material. Thus, a material having a contact angle of greater than about 75 degrees is considered hydrophobic, and a material having a contact angle of less than about 75 degrees is considered hydrophilic. Absolute values of hydrophobicity/hydrophilicity are not generally important, but relative values are.

As used herein, the term "tampon" refers to any type of absorbent structure that can be inserted into the vaginal cavity or other body cavity, such as, e.g., for the absorption of fluid, to aid in wound healing, and/or for the delivery of materials, such as moisture or active materials such as medicaments.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

Figure 2:
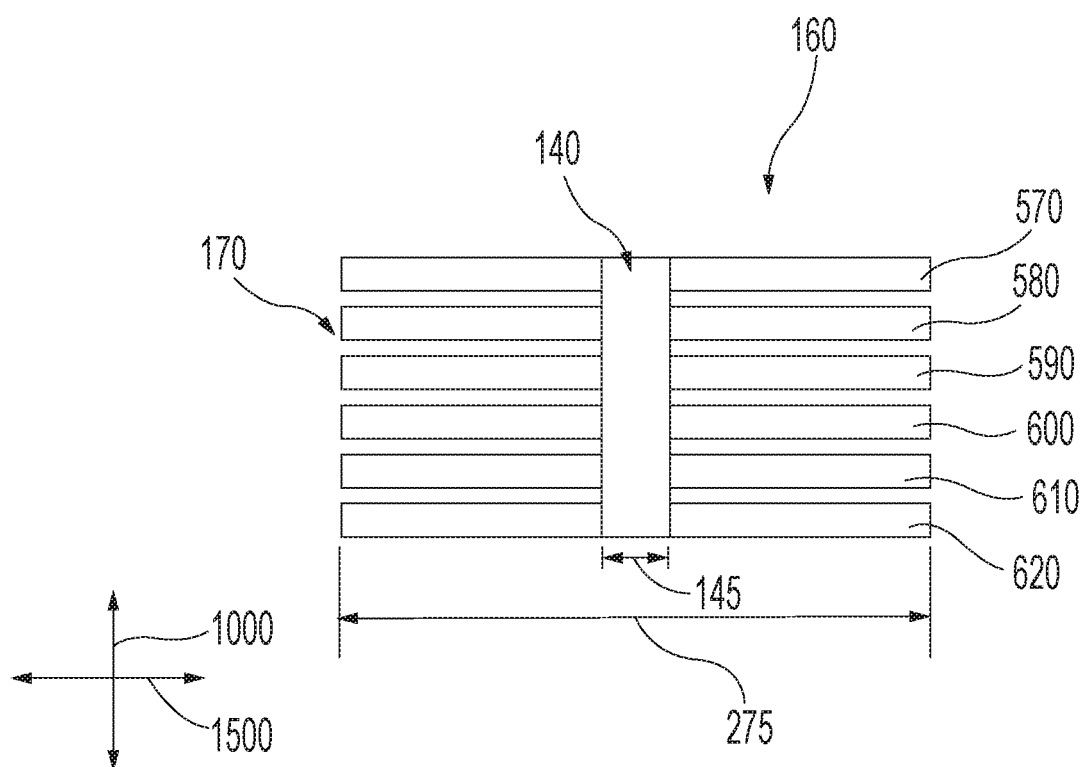
FIG. 2 is a cross-sectional view of the tampon of FIG. 1 taken along line 2-2.
Figure 3:
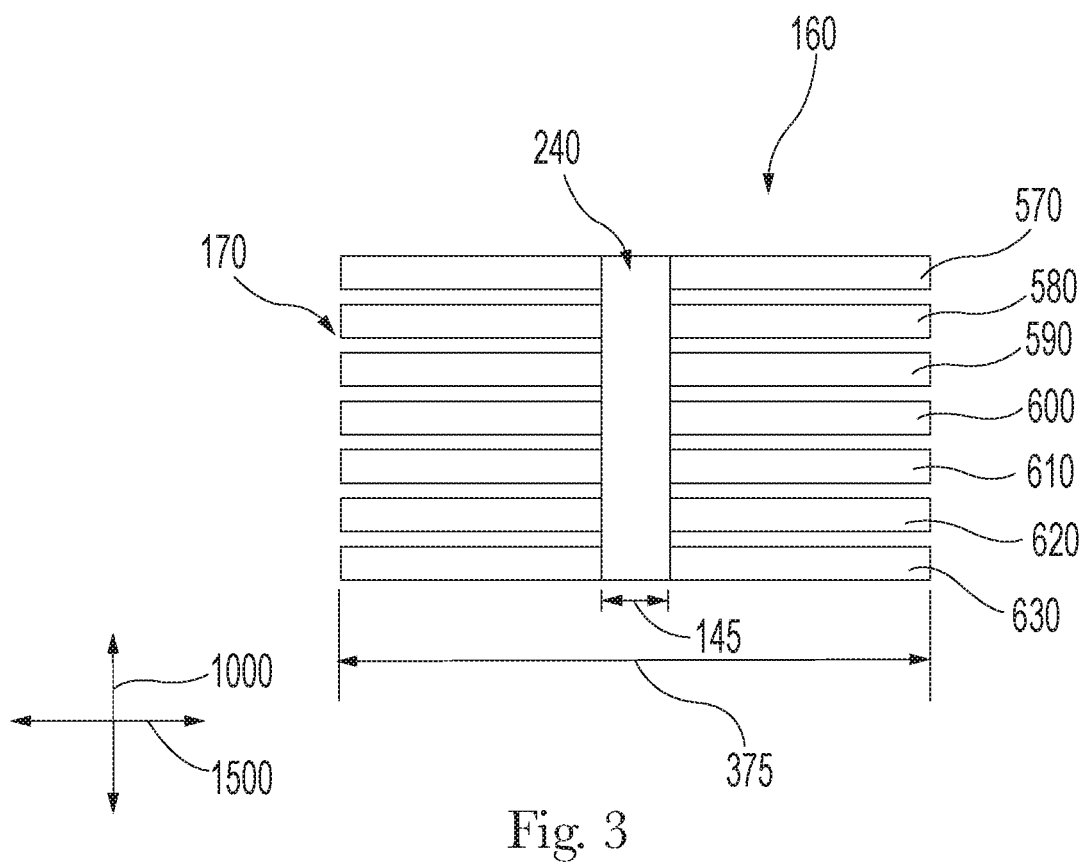
FIG. 3 is a cross-sectional view of a tampon showing another embodiment of the present invention.

The present invention relates to a tampon comprising an absorbent material which can improve performance and may, in some embodiments, improve comfort for the wearer. For ease of reference, as shown in FIGS. 1 through 3, for tampons constructed in accordance with the present invention, a longitudinal direction 1500 shall refer to a direction extending generally parallel to the maximum length of the tampon in the compressed state. And, a z-direction 1000 shall refer to a direction extending generally perpendicular to the longitudinal direction 1500 and is associated with the thickness of the tampon. A lateral direction 1750 is generally parallel to a width of the tampon as measured between opposite longitudinal edges of the tampon.

Referring to FIG. 1, a tampon 100, constructed in accordance with one embodiment of the present invention, is depicted in an expanded state. The longitudinal axis 1010 is generally parallel to the longitudinal direction 1500. The longitudinal axis 1010 may bisect a width of the tampon 100 as measured from a first longitudinal edge 1010A to a second longitudinal edge 1010B.

The tampon 100 comprises an absorbent member 160 and a withdrawal line 150. The absorbent member 160 has an insertion area 110, a withdrawal area 120, and an intermediate area 130. The intermediate area 130 is disposed between the insertion area 110 and the withdrawal area 120 and connects the insertion area 110 and the withdrawal area 120. The insertion area 110, withdrawal area 120 and intermediate area 130 may each make up about a third of the length of the absorbent member 160 in some forms. However, in other forms, the withdrawal area 120 may make up less than 20 percent of the length of the absorbent member 160, less than 15 percent of the length of the absorbent member 160, or less than about 10 percent of the length of the absorbent member 160.

The absorbent member 160 further comprises an attachment area 140. The withdrawal line 150 is attached to the absorbent member 160 in the attachment area 140. The withdrawal line 150 is attached to the absorbent member 160 and graspable by the user for removal of the tampon 100 after use. The withdrawal line 150 may be attached to at least the absorbent member 160 and extends beyond the withdrawal area 120. As shown, in some embodiments, the attachment area 140 may be generally co-linear with the longitudinal axis 1010. However, embodiments are contemplated where the attachment area 140 is generally parallel to the longitudinal axis 1010 but laterally offset therefrom. In additional embodiments, the attachment area 140 may be linearly and/or angularly displaced with respect to the longitudinal axis 1010.

As shown, the attachment area 140 may extend from the insertion area 110 to the withdrawal area 120. Embodiments are contemplated where the attachment area 140 is limited to the insertion area 110 and/or the withdrawal area 120. Additionally, embodiments are contemplated where the attachment area 140 is limited to the intermediate area 130 and/or the insertion area 110 or the withdrawal area 120.

With regard to FIG. 2, the absorbent member 160 comprises absorbent material 170 which comprises a plurality of fiber integrated nonwoven layers. As shown, in some embodiments, the absorbent material 170 may comprise six fiber integrated nonwoven layers, 570, 580, 590, 600, 610, and 620. Referring to FIG. 3, in some embodiments, the absorbent material 170 may comprise seven fiber integrated nonwoven layers, 570, 580, 590, 600, 610, 620 and 630. In some embodiments, the absorbent material 170 may comprise additional fiber integrated nonwoven layers. For example, embodiments are contemplated where the absorbent material 170 comprises greater than 7 layers, greater than 8 layers, greater than 9 layers, greater than 10 layers, greater than 11 layers, greater than 12 layers, greater than 13 layers, greater than 14 layers, greater than 15 layers, greater than 16 layers, greater than 17 layers, greater than 18 layers, greater than 19 layers, and/or less than 20 layers, less than 19 layers, less than 18 layers, less than 17 layers, less than 16 layers, less than 15 layers, less than 14 layers, less than 13 layers, less than 12 layers, less than 11 layers, less than 10 layers, less than 9 layers, or less than 8 layers. Additionally, embodiments are contemplated where the number of layers is less than 6. For example, in some embodiments, the absorbent material 170 may comprise 5 layers, less than 4 layers, less than 3 layers, or 2 layers.

In some embodiments, each of the plurality of fiber integrated nonwoven layers is homogeneous and each comprises homogenous fibers. For example, each fiber integrated nonwoven layers may comprise 100 percent viscose rayon. However, embodiments, are contemplated where each of the plurality of fiber integrated nonwoven layers comprises a blend of cotton and rayon. As an example, each of the plurality of fiber integrated nonwoven layers may comprise about 20 percent cotton and about 80 percent rayon, about 30 percent cotton and about 70 percent rayon, about 40 percent cotton and about 60 percent rayon, or about 50 percent cotton and about 50 percent rayon. Additional examples include about 20 percent rayon and about 80 percent cotton, about 30 percent rayon and about 70 percent cotton, or about 40 percent rayon and about 60 percent cotton. Other percentages encompassed by the values stated above as well as other ranges encompassed by the values stated above are contemplated.

Additional embodiments are contemplated where each of the plurality of fiber integrated nonwoven layers of absorbent material 170 comprise a percentage of plastic fiber. For example, each of the plurality of fiber integrated nonwoven layers of absorbent material 170 may comprise plastic fibers selected from at least one of polypropylene, polyethylene, polyethylene teraphthalate, poly lactic acid, and the like. For those embodiments where the fiber integrated nonwoven layers comprise plastic fiber, each of the plurality of fiber integrated nonwoven layers of absorbent material 170 may comprise about 1 percent to about 50 percent of plastic fibers, from about 5 to about 25 percent, or from about 10 to about 20 percent. The addition of plastic fibers may aid the transfer/movement of menses from one area to another of the absorbent material 170.

In one exemplary embodiment, each of the plurality of fiber integrated nonwoven layers may have a basis weight of about 100 grams per square meter ("gsm"). In some embodiments, each of the plurality of fiber integrated nonwoven layers may be at a basis weight of greater than about 20 gsm, greater than about 30 gsm, greater than about 40 gsm, greater than about 50 gsm, greater than about 60 gsm, greater than about 70 gsm, greater than about 75 gsm, greater than about 80 gsm, greater than about 85 gsm, greater than about 90 gsm, greater than about 95 gsm, greater than about 100 gsm, greater than about 110 gsm, greater than about 120 gsm, greater than about 130 gsm, greater than about 140 gsm, greater than about 150 gsm, greater than about 160 gsm, greater than about 170 gsm, greater than about 180 gsm, greater than about 190 gsm, or less than about 200 gsm or any ranges encompassed by these values and/or any number within these values.

In some embodiments, the cumulative basis weight of the absorbent material 170 may be between about 200 gsm and 1200 gsm. In some embodiments, the cumulative basis weight of the absorbent material 170 may be greater than about 200 gsm, greater than about 300 gsm, greater than about 400 gsm, greater than about 500 gsm, greater than about 600 gsm, greater than about 700 gsm, greater than about 800 gsm, greater than about 900 gsm, greater than about 1000 gsm, greater than about 1100 gsm, or less than or equal to about 1200 gsm. Embodiments are contemplated wherein the cumulative basis weight of the absorbent material 170 comprises a range encompassed by the values above and/or wherein the cumulative basis weight of the absorbent material 170 is a number within the values provided above.

As stated previously, the absorbent material 170 comprises a plurality of fiber integrated nonwoven layers. In some embodiments, each fiber integrated nonwoven layer may be created via hydroentangling. In other embodiments, each of the plurality of fiber integrated nonwoven layers may be created via mechanical processing. A suitable example of mechanical processing is needlepunching. As another example, the fiber integrated nonwoven layers may each comprise a spunlace nonwoven. Spunlace nonwoven materials may be carded and subsequently hydroentangled. As each of the layers is hydroentangled or in some embodiments needlepunched, each layer is individually fiber integrated prior to becoming a constituent of the absorbent material 170.

As shown, the attachment area 140 provides strength and integrity to the tampon 100 by attaching each of the fiber integrated nonwoven layers to adjacent fiber integrated nonwoven layers. In some embodiments, the fiber integrated nonwoven layers may be sewn together in the attachment area 140 such that the fiber integrated nonwoven layers are fiber integrated in the attachment area 140. Within each fiber integrated nonwoven layer, strength and integrity is provided via fiber integration and Z-direction fiber entanglement. However, between the fiber integrated nonwoven layers, excepting the attachment area 140, no fiber integration is provided. And as shown, the attachment area 140 is disposed laterally inboard of the longitudinal edges 1040A and 1040B. Accordingly, no fiber integration is present outboard of the attachment area 140 between the fiber integrated nonwoven layers.

The absorbent member 160 is compressed and placed into an insertion device prior to use. During compression, fibers of one fiber integrated nonwoven layer may intermingle with fibers of adjacent fiber integrated nonwoven layers to some extent. However, conventional compression pressures should not be sufficient to detract from the performance of the absorbent material 170. Accordingly, fiber integration does not include fiber intermingling which is created from compressing the absorbent material 170 and/or calendar bonding the absorbent material 170.

The fiber integrated nonwoven layers may be attached to one another in the attachment area 140 by any suitable method. As an example and as stated previously, the fiber integrated nonwoven layers may be attached to one another in the attachment area 140 by being sewn together. When sewn together, thread is integrated into each of the fiber integrated nonwoven layers attaching each of the fiber integrated nonwoven layers together. In contrast, constituent fibers of each of the fiber integrated nonwoven layers are integrated within only their respective layers.

Without wishing to be bound by theory, it is believed that because the layers of nonwoven material are provided with fiber integration between adjacent layers only in the attachment area 140, the layers of nonwoven material expand more freely and more easily than absorbent material of conventional tampons. In order to provide integrity to the absorbent material of conventional tampons, many provide fiber integration across the entire thickness of the absorbent material and across the entire width of the tampon, i.e. fiber integration between adjacent layers. The conventional use of fiber integration of the absorbent material is believed to inhibit the expansion and movement of the absorbent material. Alternatively, some may provide structural integrity to layers of absorbent material via fusion bonding. Such bonding is believed to inhibit the movement/expansion of the absorbent material which can result in reduced performance.

In contrast, and as stated previously, the fiber integration provided for each nonwoven layer provides structural integrity of each of the individual nonwoven layers. And, the attachment area 140 provides structural integrity to the absorbent member 160. Because each of the fiber integrated layers comprise no fiber integration outboard of the attachment area 140 and because each of the fiber integrated layers are attached in the attachment area 140, it is believed that the expansion/movement of each of the fiber integrated nonwoven layers is less inhibited than absorbent material of conventional tampons.

As shown in FIGS. 2 and 3, a width 145 of the attachment area 140 does not extend a full width 275 or 375 of a tampon constructed in accordance with the present invention. In some embodiments, the width 145 of the attachment area 140 may be about 3 mm or about 8 mm. In some embodiments, the width 145 of the attachment area can be less than about 25 mm, less than about 20 mm, less than about 15 mm, less than about 10 mm, less than about 5 mm, or less than about 3 mm, or greater than or equal to about 1 mm. Embodiments are contemplated where the width 145 is within a range encompassed by the values above or is a number that is encompassed by the values above.

In another embodiment, the width 145 of the attachment area 140 may vary. As an example, the width 145 of the attachment area 140 adjacent the insertion area 110 (shown in FIG. 1) may be different than the width 145 of the attachment area 140 adjacent the withdrawal area 120 (shown in FIG. 1). As an example, adjacent the insertion area 110, the width 145 of the attachment area 140 may be less than the width 145 of the attachment area 140 adjacent the withdrawal area 120. In another embodiment, the width 145 of the attachment area 140 adjacent the insertion area 110 may be greater than the width 145 of the withdrawal area 120. In still other embodiments, the width 145 of the attachment area 140 may be different in the intermediate area 130 (shown in FIG. 1) than the width 145 of the attachment area 140 of either the insertion area 110 and/or the withdrawal area 120. Embodiments are contemplated where the width 145 of the attachment area 140 is varied in combination with the positioning of the attachment area 140 as discussed previously.

The width 275 or 375 of the tampon in an unrolled and/or unfolded state can be from about 30 mm to about 120 mm or about 50 mm to about 70 mm, including all numbers within these ranges and any ranges formed thereby, in some embodiments. In some embodiments, the attachment area 140 may be disposed greater than about 20 mm laterally inboard of the longitudinal edges 1040A/1040B. In some embodiments, the attachment area 140 may be disposed greater than about 25 mm laterally inboard, 30 mm laterally inboard, or 35 mm laterally inboard of the longitudinal edges 1040A and 1040B.

Surprisingly, the inventors have found that when the absorbent material 170 comprises layers, where each layer is 100 gsm spunlace nonwoven material, with 100% viscose rayon fibers, the cross sectional areas (in a compressed state) of the absorbent member 160 can be less than that of conventional tampons. Table 1 shows a comparison of the compressed cross sectional areas of a currently marketed tampon versus the compressed cross sectional area of tampons constructed in accordance with FIGS. 2 and 3. The compressed cross sectional area was taken after being removed from the applicator and within a few minutes of being removed from the applicator.

TABLE 1

| Product Description | Diameter (mm) | Compressed Cross Sectional Area (square mm) | % Area Reduction |
| --- | --- | --- | --- |
| Currently marketed - Tampax Pearl Super | 14.93 | 175.07 | 0% |
| 100 gsm, 100% viscose rayon - 6 layers | 14.56 | 166.50 | 5% |
| 100 gsm, 100% viscose rayon - 7 layers | 14.49 | 164.90 | 6% |

The smaller cross sectional areas are believed to provide more comfort during insertion of the tampon. Additionally, from a macro viewpoint, the smaller cross sectional areas could reduce applicator size. The reduction of applicator size could in turn reduce the cost as well as the amount of packaging utilized for individual tampons. This could in turn result in a reduction in the amount of packaging for the tampon box comprising a plurality of tampons and for the box comprising a plurality of tampon boxes, etc.

Additionally, even with the smaller—prior to use—cross sectional area, the experimental tampons performed well with regard to the FDA syngyna specification.

TABLE 2

| Product Description | Syngyna (g) | Dry tampon weight (g) |
| --- | --- | --- |
| Currently marketed - Tampax Pearl Super | 11.3 | 2.84 |
| 6 layers each of 100 gsm, 100% viscose rayon | 10.78 | 2.47 |
| 7 layers each of 100 gsm, 100% viscose rayon | 11.87 | 2.80 |

As shown in Table 2, the seven layer embodiments of 100 gsm spunlace, 100% viscose rayon, performed better on the syngyna test than did the conventional tampons tested. The syngyna method is disclosed hereafter. The efficiency of the 6 layer and 7 layer experimental products was 4.36 g syngyna/g of fiber and 4.23 grams syngyna/grams of fiber, respectively. In contrast, the conventional efficiency was 3.98 g of syngyna/g of fiber.

Another benefit of the absorbent material 170 of the present invention is that regardless of the configuration, e.g. 6 layers or 7 layers, each has a dry weight less than that of a comparable conventional tampon.

Figure 4A:
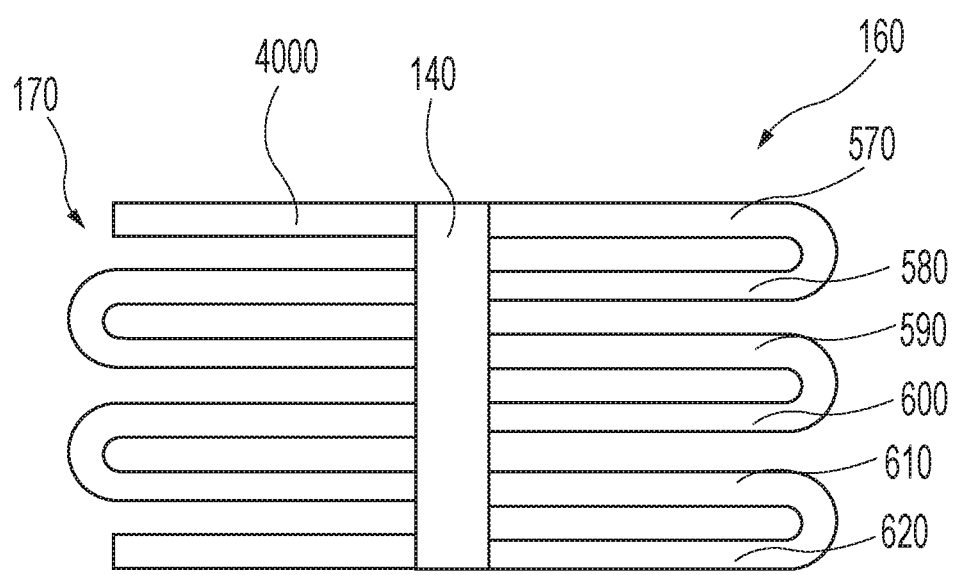
FIGS. 4A-4C are cross-sectional views of tampons constructed in accordance with the present invention.

As shown in FIG. 4A, forms of the present invention are contemplated where the plurality of fiber integrated layers comprises a single nonwoven web 4000. For example, the first layer 570, second layer 580, third layer 590, fourth layer 600, fifth layer 610, and sixth layer 620 may each be part of the same nonwoven web. As shown, the nonwoven web 4000 may be folded a plurality of times to form each of these layers. Additional forms are contemplated where a plurality of nonwoven webs are utilized and folded at least once to form a plurality of layers. Examples are provided in FIGS. 4B and 4C.

Figure 4B:
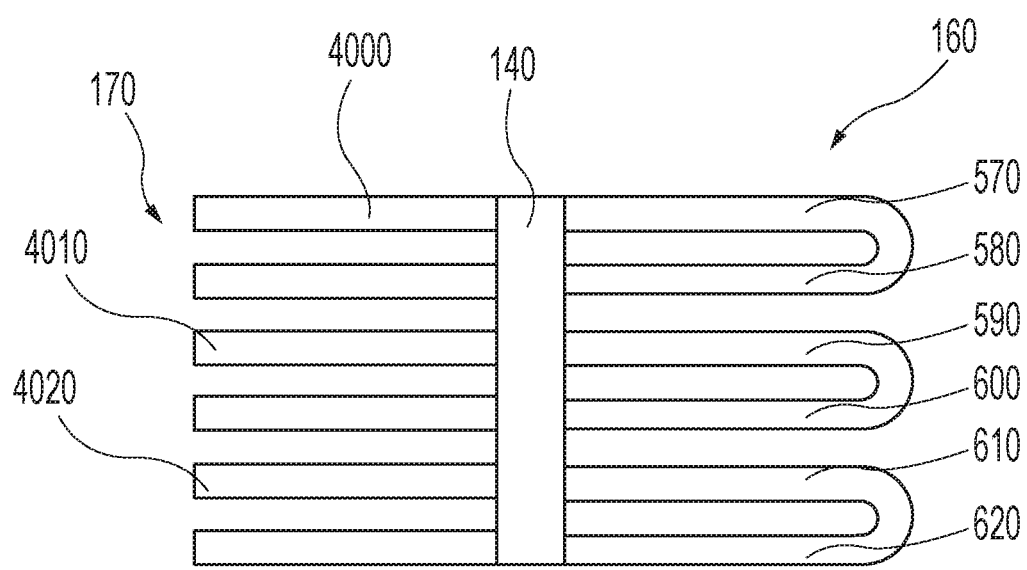
Figure 4C:
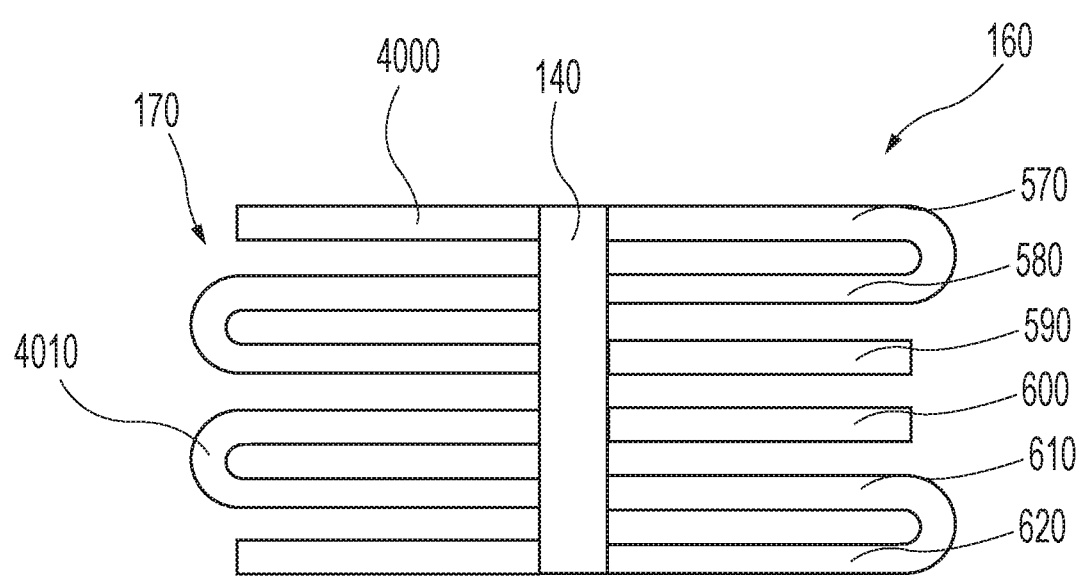

As shown in FIG. 4B, a plurality of nonwoven webs, 4000, 4010, 4020 may be utilized to form the plurality of layers. As shown, in some forms of the present invention, three nonwoven webs may be utilized where each may form at least two layers. Other forms are contemplated. For example, two nonwoven webs 4000 and 4010 may be utilized where each of the nonwoven webs may form at least three layers.

Additionally, it is believed that the loft of the individual layers can impact the performance of the absorbent material 160. It is believed that recovery after compression for those layers with lower loft may be inhibited. In contrast, for those layers with greater loft prior to compression would experience better recovery in use. Loft of the individual layers can be greater than about 0.95 mm, greater than about 1.0 mm, greater than about 1.1 mm, greater than about 1.2 mm, greater than about 1.3 mm, greater than about 1.4 mm, or greater than about 1.5 mm, specifically including all values within these ranges and any ranges created thereby.

Tampons of the present invention may be processed in a variety of manners. In one embodiment, the absorbent material 170 may be acquired by a supplier such as Sandler AG. Alternatively, the absorbent material may be manufactured from fibers. In general fiber processing requires obtaining a bale of fibers suitable for use as the absorbent material 170. As stated previously, fibers may include cotton, rayon, plastic, or combinations thereof. In one embodiments, a bale cutter breaks apart the fibers and provides the fibers to a fiber carding machine or turbo carding machine. The fiber carding machine cards the fibers. Note that an unbonded carded nonwoven web typically has little to no strength in the CD or z-direction. In order to achieve the desired basis weight, a plurality of unbonded carded nonwoven web may be combined into a single nonwoven web. The unbonded carded nonwoven web(s) may be provided to a hydroentangling device or a needlepunch device, each of which are known in the art. Other manufacturing processes which can entangle fibers of the carded webs may also be utilized. As stated previously, via hydroentangling or needlepunching, the carded nonwoven web(s) are combined via fiber entanglement which provides strength to resultant web thereby creating a nonwoven web. This process may be repeated a plurality of times to produce the desired number of fiber integrated nonwoven layers in the absorbent material 170. The nonwoven materials of the present invention may be turbo carded.

Carding of nonwovens typically orients fibers in a desired direction. Typically the fiber orientation is in the machine direction. Subsequent mechanical processing, e.g. hydroentangling or needlepunching, provides Z-direction integration of the fibers and does not substantially change the initial fiber orientation.

Forms of the present invention are contemplated where fiber orientation is substantially in the cross machine direction. By "substantially" it is meant that when viewed under microscope, a majority of fibers of a sample nonwoven, e.g. sample absorbent material of a tampon in question, would be oriented in the cross machine direction (perpendicular to the walls of the applicator in which the absorbent was housed). Other forms are contemplated where the fiber orientation is substantially in the machine direction.

As stated above, the nonwoven material for the fiber integrated nonwoven layers may be purchased and provided on a roll to a converting line or produced internally and provided to the converting line. The provided nonwoven material may be cut and layers of the provided nonwoven material are stacked to form the absorbent material 170. The withdrawal line 150 (shown in FIG. 1) is provided to the converting line. The withdrawal line 150 is attached to the absorbent material 170 which can also attach adjacent fiber integrated nonwoven layers in the attachment area 140. Alternatively, the fiber integrated nonwoven layers may be fiber integrated and/or attached separate from the attachment of the withdrawal line 150.

As an optional step, prior to and/or after attaching the withdrawal line 150, the plurality of layers of nonwoven material may be calendared to ensure that appropriate thickness prior to packaging. The calendar rolls may be heated to provide light bonding between the fiber integrated nonwoven layers within and/or external to the attachment area 140. Such light bonding is believed to be relatively weak and provide little to no restriction in the movement/expansion of the fiber integrated nonwoven layers with respect to one another. Such light bonding is not considered to be fiber integration.

Subsequently, the absorbent material 170 comprising the plurality of fiber integrated nonwoven layers may be compressed and pushed into an applicator. Much like calendaring, the compression of the plurality of fiber integrated nonwoven layers may create light bonding between adjacent fiber integrated nonwoven layers; however, such light bonds are believed to be relatively weak and provide little to no restriction in the movement/expansion of the fiber integrated nonwoven layers. Again, such light bonding is not considered to be fiber integration.

Pressures and temperatures suitable for compression are well known in the art. Typically, the absorbent material and the fluid pervious overwrap are compressed in the radial direction and optionally axially by any means well known in the art. While a variety of techniques are known and acceptable for these purposes, a tampon compressor machine available from Hauni Machines, Richmond, Va., is suitable.

Referring to FIGS. 1-4C, in some embodiments, the absorbent material 170 may be surrounded, at least in part, by an overwrap. For those embodiments, with an overwrap, the overwrap may surround at least the intermediate area 130 of the absorbent material 170 and may in some embodiments, cover the insertion area 110 and/or the withdrawal area 120. In some embodiments, the overwrap may extend beyond the withdrawal area 120 and create a skirt around the absorbent material 170.

In some embodiments, the overwrap may be attached to the absorbent material 170 in the attachment area 140 and unattached everywhere else. In some embodiments, the overwrap may be attached to the absorbent material 170 in the attachment area 140 and may be attached to the absorbent material 170 via fusion bonds. In such embodiments, the overwrap may comprise fibers with a lower melting temperature than that of the absorbent material 170. So the fusion bonds are only created with regard to the overwrap and not the absorbent material 170.

For those embodiments including overwraps, the overwrap may comprise a masking region and a wicking region. In other embodiments two separate overwraps (a masking overwrap which becomes a masking region and a wicking overwrap which becomes wicking region) may be provided to form the final overwrap (which may or may not be joined). Whether it is a masking region or a "separate" masking overwrap, the masking material may be hydrophobic or may be treated to render the region or overwrap hydrophobic if the starting if material is hydrophilic. Treatments that render a material hydrophobic include but are not limited to applying to or dipping the material in silicones, fatty acids (such as sucrose ester fatty esters), fluorocarbons, such as SCOTCHGUARD, and waxes. Whether it is a wicking region or a wicking overwrap, the wicking material may be hydrophilic or may treated to render the region or overwrap to be hydrophilic if the starting material is hydrophobic. Treatments that render a material hydrophilic include but are not limited to applying or dipping the material in surfactants, including non-ionic surfactants.

In other embodiments where two pieces of material are used to form the overwrap, a masking material/region/overwrap may be joined to a wicking material/region/overwrap by sewing, adhesives, bonding including thermally bonding, pressure fusion bonding, or any other suitable means known in the art for joining such materials. Alternatively, the two materials used to create the overwrap may not be physically connected at all.

In some embodiments, the absorbent member 160 may be compressed prior to application of the overwrap onto the absorbent member 160. In such embodiments, the overwrap may be positioned on the compressed absorbent member such that the wicking region/overwrap covers at least a portion of the exterior surface of the compressed absorbent member proximal to the withdrawal end and the masking region/overwrap surrounds at least a portion of the exterior surface of the compressed absorbent member proximal to the insertion end. In some embodiments, the wicking region/overwrap extends beyond the withdrawal end of the compressed absorbent member to define a skirt portion. In embodiments that begin with providing a compressed absorbent member, the overwrap, comprising both the wicking region/overwrap and the masking region/overwrap, may be joined or applied to the compressed absorbent member subsequent to compression. Alternatively, a wicking overwrap may be applied prior to compression (discussed further below) and a masking overwrap may be applied subsequent to compression. Overwraps applied subsequent to compression should be extensible such that the tampon will be able to expand within the vagina. The overwrap may be made extensible by processes such as, ring rolling, creping, MICREXing, and SELFing as described in U.S. Pat. No. 5,518,801 issued to Chappell on May 21, 1996, incorporated herein by reference.

The optional overwrap material is liquid permeable via natural liquid pathways or aperturing. Exemplary overwrap materials include non-wovens comprising a blend of synthetic and natural fibers, and polymeric films. The synthetic fibers may include, but are not limited to, fibers such as polyester, polyolefin, nylon, polypropylene, polyethylene, polyacrylic, cellulose acetate, or bicomponent fibers. Natural fibers may include, but are not limited to, those commonly known to be non-synthetic and of natural origin such as cotton and/or rayon. Polymeric films can comprise polyolefins and polyesters, for example. Depending on their intended use, the polymeric films may be made liquid permeable through aperturing or other "opening" technique.

The withdrawal line 150 of the present invention could be joined to the absorbent member 160 and graspable by the user for removal after use. Any of the withdrawal lines currently known in the art, such as string, may be used as a suitable withdrawal mechanism. In addition, the withdrawal lines can take on other forms such as a ribbon, loop, tab, or the like. The withdrawal line may be integral with the absorbent material. In some embodiments, the withdrawal line may be discrete and non-integral with the absorbent material or optional overwrap.

The withdrawal line may be attached in any suitable manner known in the art including sewing, adhesive attachment, or a combination of known bonding methods. The withdrawal line may be joined to any suitable location on the tampon.

The withdrawal line material and configuration can vary. A fibrous string is an exemplary embodiment of the withdrawal line. The withdrawal line can comprise any suitable synthetic material, natural material, or blends thereof. Suitable synthetic materials include, for example, non-natural material, such as, for example, polyethylene, polypropylene, polyethylene-polypropylene copolymer, polyvinyl alcohol, polyvinyl acetate, polyester, nylon, polylactides, polyhydroxylalkanoates, aliphatic ester polycondensates, cellulose acetate, and mixtures thereof. Such fibers can be formed in any suitable manner, such as, e.g., by melt spinning to produce staple fibers, monofilaments, multifilaments, continuous filaments, or other fibers useful in forming a withdrawal string. Fiber formation and processing generally includes the addition of finish compositions, such as, for example, lubricants and anti-statics.

The withdrawal line can be any suitable construction. For example, in certain embodiments, the withdrawal line can be a twisted or knitted construction containing multiple plies of yarn. The plies of yarn can be formed from twisted staple fibers or multiple continuous filaments. In addition, or alternatively, the weight or count of the yarn and/or the number of plies can be any weight or plies suitable for providing the desired strength, aesthetics, grippability, wearing comfort, handling, cost, and/or processing. In certain embodiments, the withdrawal line can be formed from 6 twisted plies of 10 count polypropylene yarn, one knitted ply of 10 count polypropylene yarns, or any other suitable construction.

The withdrawal line fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

Test Methods

Syngyna Test

The Syngyna test is carried out as described in 21 CFR § 801.430(f)(2).

What is claimed is:

1. A tampon comprising:
    an absorbent member comprising an insertion area, a withdrawal area, an intermediate area between the insertion area and the withdrawal area, and an attachment area,
    the absorbent member comprising a plurality of discrete nonwoven layers in a stacked and layered configuration,
    wherein each of the stacked nonwoven layers extends along a plane along a longitudinal direction parallel with a longitudinal axis of the absorbent member, and a lateral direction perpendicular to the longitudinal direction; and wherein the nonwoven layers are stacked along a z-direction perpendicular to the plane, and
    wherein the stacked nonwoven layers are sewn together in the attachment area to form a unitary stack including all of the layers, such that two or more of the nonwoven layers are fiber integrated with an adjacent nonwoven layer via the sewing in the attachment area, and not fiber integrated to an adjacent nonwoven layer in areas outboard of the attachment area; and
    a withdrawal line extending from the withdrawal area and attached to the absorbent member in the attachment area.

2. The tampon of claim 1, wherein each of the nonwoven layers comprises a hydroentangled nonwoven having a basis weight of greater than 75 grams per square meter.

3. The tampon of claim 1, wherein the absorbent member comprises from between 2 fiber integrated nonwoven layers and 20 fiber integrated nonwoven layers, and wherein each of the fiber integrated nonwoven layers has a basis weight of between about 20 grams per square meter to about 600 grams per square meter.

4. The tampon of claim 1, wherein the absorbent member comprises from between 4 fiber integrated nonwoven layers and 8 fiber integrated nonwoven layers, and wherein each of the fiber integrated nonwoven layers have a basis weight of between about 30 grams per square meter to about 250 grams per square meter.

5. The tampon of claim 1, wherein the absorbent member comprises at least 7 fiber integrated nonwoven layers and wherein each of the fiber integrated nonwoven layers comprise a basis weight of between about 75 grams per square meter to about 120 grams per square meter.

6. The tampon of claim 1, wherein each of the fiber integrated nonwoven layers is needlepunched and has a basis weight of greater than 75 grams per square meter.

7. The tampon of claim 6, wherein the absorbent member comprises at least 5 fiber integrated nonwoven layers.

8. The tampon of claim 6, wherein the absorbent member comprises at least 6 fiber integrated nonwoven layers.

9. The tampon of claim 6, wherein the absorbent member comprises at least 7 fiber integrated nonwoven layers.

10. The tampon of claim 1, wherein each of the plurality of fiber integrated nonwoven layers comprises a blend of cotton and rayon fibers.

11. The tampon of claim 10, wherein each of the plurality of fiber integrated nonwoven layers comprises plastic fibers.

12. The tampon of claim 6, wherein each of the plurality of fiber integrated nonwoven layers has a basis weight of between about 75 grams per square meter to about 120 grams per square meter.

13. The tampon of claim 1 further comprising an overwrap which surrounds at least the intermediate area.

14. A method of producing a tampon comprising the steps of:

providing a plurality of discrete nonwoven layers each having a basis weight of greater than 75 grams per square meter;

stacking the nonwoven layers along a z-direction to form a layered configuration, whereby each of the stacked nonwoven layers extends along a plane along a longitudinal direction parallel with a longitudinal axis of the tampon when completed, and a lateral direction perpendicular to the longitudinal direction, the z-direction being perpendicular to the plane;

providing a withdrawal line; and sewing the nonwoven layers together in an attachment area such that one or move adjacent nonwoven layers in the stack are fiber integrated in the attachment area, to form a unitary absorbent member comprising the nonwoven layers, and attaching the withdrawal line to the absorbent member in the attachment area, and wherein one or more of the nonwoven layers is not fiber integrated with another of the nonwoven layers in areas outboard of the attachment area.

15. The method of claim 14, wherein each of the nonwoven layers has a basis weight of greater than 75 grams per square meter to about 120 grams per square meter.

* * * * *